US006627321B1

(12) United States Patent
Ellingsen et al.

(10) Patent No.: US 6,627,321 B1
(45) Date of Patent: Sep. 30, 2003

(54) IMPLANTS WITH MODIFIED SURFACES FOR INCREASED BIOCOMPATIBILITY, AND METHOD FOR PRODUCTION THEREOF

(75) Inventors: Jan Eirik Ellingsen, Bekkestua (NO); Ketil Videm, Oslo (NO); Lars Opsahl, Askim (NO); Hans Jacob Ronold, Oslo (NO)

(73) Assignee: Astra Tech AB, Molndal (SE)

( * ) Notice: Subject to any disclaimer, the term of this patent is extended or adjusted under 35 U.S.C. 154(b) by 0 days.

(21) Appl. No.: 09/868,965

(22) PCT Filed: Dec. 22, 1999

(86) PCT No.: PCT/IB99/02093

§ 371 (c)(1),
(2), (4) Date: Sep. 25, 2001

(87) PCT Pub. No.: WO00/38753

PCT Pub. Date: Jul. 6, 2000

(30) Foreign Application Priority Data

Dec. 23, 1998 (SE) .............................. X9804536

(51) Int. Cl.[7] .............................. B32B 15/04; B32B 9/00
(52) U.S. Cl. .................... 428/469; 428/472.3; 428/327; 623/23.49; 623/23.57
(58) Field of Search .............................. 428/469, 472.3; 427/327; 623/23.57, 23.49

(56) References Cited

U.S. PATENT DOCUMENTS

| 4,542,539 | A | * | 9/1985 | Rowe, Jr. et al. | ......... 623/23.57 |
| 5,383,935 | A | * | 1/1995 | Shirkhanzadeh | ......... 623/23.49 |

FOREIGN PATENT DOCUMENTS

| EP | 0212929 | 8/1986 |
| EP | 0264354 | 4/1988 |

OTHER PUBLICATIONS

CRC Handbook, 68th Edition, p. D–146.*
File WPI, Derwent, "Production of internal bone implants . . . ", Univ. Sarat Tekh, No. 1997–446864. No month.

* cited by examiner

Primary Examiner—Deborah Jones
Assistant Examiner—Vivek Koppikar
(74) Attorney, Agent, or Firm—Leonard R. Stevenson; Birch, Stewart, Kolasch & Birch, LLP

(57) ABSTRACT

An implant with a surface modified for improved biocompatiability consisting of a metal or an alloy thereof, said implant surface comprising a modified outer layer is disclosed, wherein said metal preferably is titanium, zirconium, hafnium or tantalum, and most preferably titanium, and said modified outer layer preferably comprises a hydride of said metal. Also a method for the production of such an implant is disclosed.

37 Claims, 2 Drawing Sheets

IMPLANTS WITH MODIFIED SURFACES FOR INCREASED BIOCOMPATIBILITY, AND METHOD FOR PRODUCTION THEREOF

This application is the national phase under 35 U.S.C. §371 of PCT International Application No. PCT/IB99/02093 which has an International filing date of Dec. 22, 1999, which designated the United States of America and was published in English.

TECHNICAL FIELD OF THE INVENTION

The present invention relates to a biocompatible implant consisting essentially of a metal such as titanium, zirconium, hafnium and tantalum, or an alloy thereof, the surface of which has been modified in order to increase ,the biocompatibility. The invention also relates to a method modification of surfaces to.

BACKGROUND OF THE INVENTION

Titanium, zirconium, hafnium and tantalum and their alloys have a superb corrosion resistance in body fluids and are well accepted by the human body. Titanium and its alloys are therefore much used for implants. In many applications it is of utmost importance that the metal form a strong and lasting connection with the surrounding tissues and that this connection does not impair healing. This is not easy to achieve. Implant materials not giving satisfactory healing usually lead to loss of contact between the implant and tissue, often followed by complications leading to implant failure. This has given the patients severe pain and required costly medical treatment often including complicated and expensive surgery.

To deal with these problems geometric modifications of implants have been applied. Increasing the surface roughness expands the area of tissue contact. Different methods including plasma spraying, sand blasting or creation of holes or grooves to establish an inter-locking effect in the bone have achieved this. Electron beam machining has been used to make surfaces that hardly can be produced with conventional machining. These latter methods can be optimised to also give additional geometrical advantages. Another method commonly used is to apply a layer of hydroxyapatite coating onto the titanium implant surface. This mineral is present in hard tissue of all mammals. All these techniques are manufacturing- and user- sensitive and it is problematic to carry out coating in a way that gives sufficient bonding between the mineral and the metal. Another serious disadvantage with these techniques is destruction of the mineral coating during applications where stress is applied to the implant. This seriously hampers applications of metal implants.

In contact with oxygen titanium, zirconium, hafnium and tantalum and their alloys are instantaneously covered with a thin layer of oxide. Various techniques exist to increase the thickness of the oxide layer. Significant improvements have not been obtained so far, concerning the biocompatibility of the implant material. The oxide layer may be further treated. For example EP-A-0 264 354 describes a process for forming a coating of a calcium phosphate compound on the surface of the titanium oxide layer. In the process to obtain the desired oxide layer it is possible to use either acid treatment or formation of an intermediate metal hydride, which is then heated in order to obtain the desired oxide as a substrate for the calcium phosphate coating.

Another method for treating the surface of endosseous implants is to use the process described in EP-A-0 212 929, according to which a ceramic material is thermally sprayed onto the metal surface after its been roughened with an appropriate technique. The roughening of the metal surface may be obtained by e.g. thermally spraying titanium hydride onto it, but, as for EP-A-0 264 354, the titanium hydride coated implant is only an intermediate product in the process of obtaining the desired end product, in this case the ceramic coated implant.

SUMMARY OF THE INVENTION

The object of the present invention is to provide an implant with improved biocompatibility compared to known implants. This is obtained by modifying the surface of the implant. The modified surface further promotes contact between tissue ant implant. In the research work leading to the present invention it was surprisingly observed that implants coated with titanium hydride led to a better adherence between the metal and bone, compared to other titanium implants. The fact that titanium hydride coated implants could be used directly is very surprising; up to the present invention it has been considered necessary to coat hydrided surfaces to achieve satisfactory biocompatibility. In the work leading to the present invention it was demonstrated in animal models that tissues in contact with the titanium hydrided titanium surface was healthy and showed no foreign body reactions as examined by microscopy.

The present invention thus relates to biocompatible metallic implants, characterized in that the surfaces of the implants have been modified so that they comprise a metal hydride layer.

The invention also relates to a method for the production of a biocompatible implant, wherein a core of metal or an alloy thereof is coated with a surface layer of hydride.

The characterizing features of the invention will be evident from the following description and the appended claims.

DETAILED DESCRIPTION OF THE INVENTION

As stated above, the invention relates to a biocompatible implant consisting essentially of metal or an alloy thereof, characterized in that the surface of the implant is modified, preferably so that it comprises an outer layer, preferably essentially consisting of a metal hydride. The expression "biocompatible implant" used herein relates to implants suitable for introduction into the body of a mammal, and especially of a human. The implants according to the invention or implants produced with the method according to the invention are intended for introduction into all living hard and soft tissues, including bone, cartilage and teeth, and all body cavities including joints and inner ear.

The hydride layer in the implant according to the invention may be any metal hydride or a mixture of several different metal hydrides.

In the case of an implant of titanium or an alloy thereof the major part of the modified outer layer, i.e. more than 50%, is preferably constituted by $TiH_{1.924}$ or $TiH_2$. This titanium hydride layer may also comprise small amounts of other elements and hydrides thereof.

The invention also relates to a method suitable for the production of the above described biological implant. This method results in an implant surface, which comprises a layer of hydride. This may be performed either by coating with a layer of hydride, or by converting the surface into hydride. It is possible to use a commercially available implant and convert its surface to comprise a hydrided layer. It is also possible to produce the implant according to the invention, by first producing a suitably shaped core of titanium or an alloy thereof, and then accomplish the titanium hydride layer.

The method according to the invention is preferably performed by treating the starting implant or core by electrolysis. The starting implant is then placed in an electrolytic bath. During the electrolysis, the starting implant will constitute the cathode.

The electrolytic bath is preferably an aqueous solution of NaCl with acidic pH-value. The pH is preferably adjusted to the appropriate value by addition of HCl, $H_2SO_4$, $HNO_3$, $HClO_4$, or an organic acid or a mixture of two or more of these acids.

The temperature of the electrolytic bath should also be adjusted. It is possible to perform the method according to the invention at ambient temperature, i.e. at approximately 20° C., however, at this temperature the reaction rate will be very slow. In order to increase the reaction rate, the temperature should be raised, preferably to at least 40° C., and most preferably to at least 80° C.

The most preferred electrolytic solution for use in the method according to the invention is an aqueous solution comprising from 0,01 M to 1 M of a saturated salt solution and from $10^{-5}$ to 10 M of at least on of the above mentioned acids.

The current used to perform the electrolysis is 0.001–1000 $mA/cm^2$.

In order to further improve the biocompatability of the implant it is to be implanted into, it is advantageous to increase the surface roughness of the hydride layer. This can for example be done by blasting, e.g. grit blasting, before hydriding the implant.

The invention will now be further explained in the following examples. These examples are only intended to illustrate the invention and should in no way be considered to limit the scope of the invention.

BRIEF DESCRIPTION OF THE DRAWINGS

In the examples below reference is made to the accompanying drawings on which.

EXAMPLES

Example 1

Specimens of Titanium Grade 2 were carefully cleaned by ultrasonic treatment with trichlorethylene for 15 min, rinsed in ethanol, and then ultrasonic treated with ethanol for 10 min. This was repeated three times, and the specimens were then rinsed in water. The clean specimens were then cathodically polarized in a bath consisting of 0.5 M NaCl and 1 M HCl. The presence of a titanium hydride after the electrolysis was confirmed by X-ray diffraction analysis.

The electrolysis was performed at different temperatures, 25° C. and 80° C., in order to study the influence of the temperature on the obtained titanium hydride layer, and also at different pH-values, pH 0 and pH 2, in order to study the influence of the pH.

Figure 1:
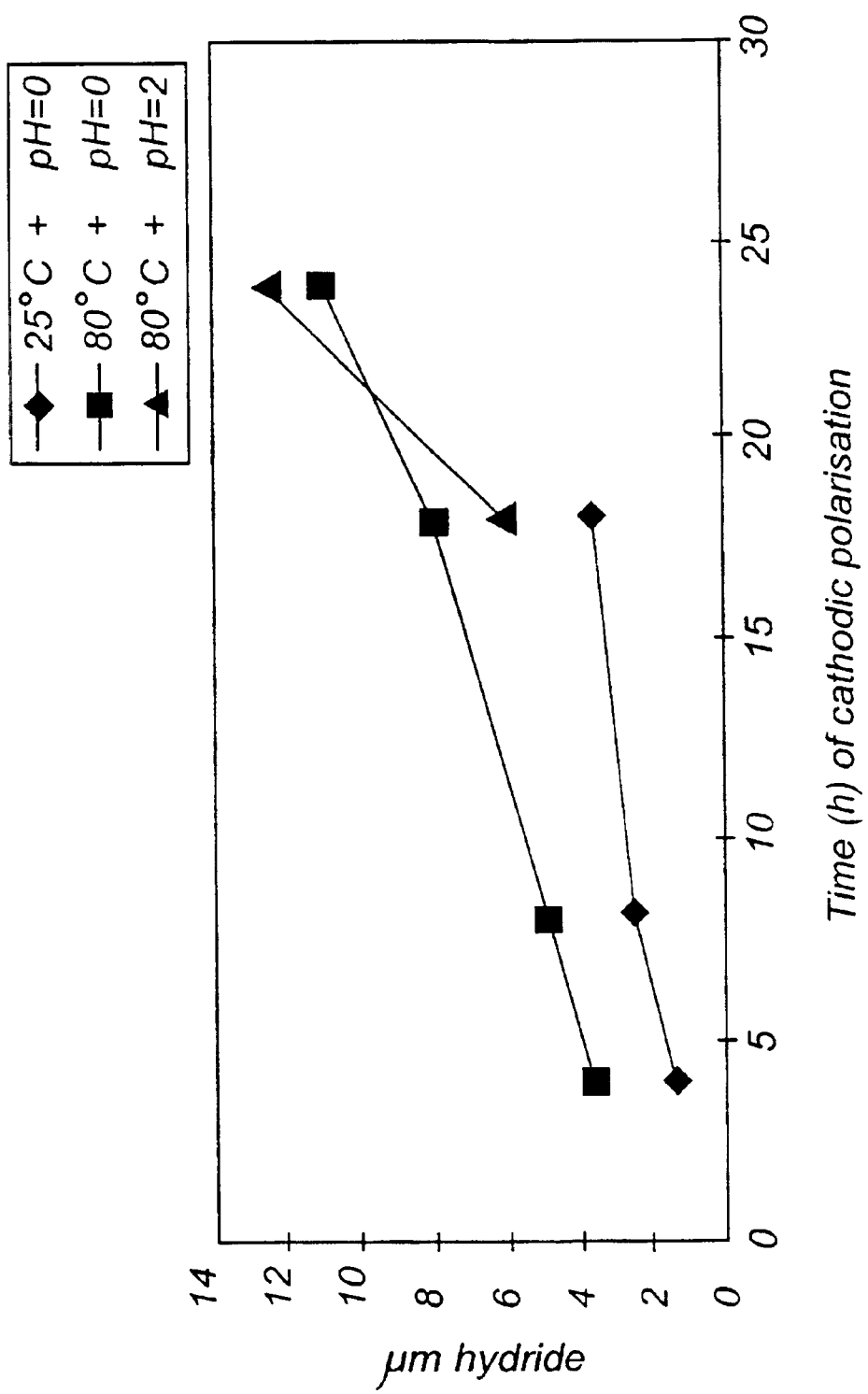
FIG. 1 illustrates the thickness of titanium hydride layers obtained by electrolysis of titanium implants at different temperatures and pH-values (see Example 1)

The thickness of the obtained titanium hydride layer was determined by microscopy of metallographic cross sections. The thickness as a function of the time used for the treatment is shown in FIG. 1.

As evident from the figure, it is preferable to use a temperature of 80° C. compared to a temperature of 25° C.

Example 2

Experimentally produced implants were made of titanium grade 2. The implants were threaded and had a diameter of 3.5 mm and a length of 4.5 mm. The implants were made to fit the bones of rabbits. The implants were treated for 18 hours in the same bath and under the same conditions as used in example 1. After sterilization by autoclaving, these implants (Implants of the invention) were introduced by surgery in the femurs of four rabbits. These rabbits were reproduced with special care to render animals with very similar genetics.

For comparison, implants that were only cleaned and autoclaved (Reference implants) were introduced in similar positions in the rabbits.

Three implants with titanium hydride layers and two with cleaned and autoclaved surface were present in each rabbit. The rabbits were euthanized after 8 weeks. The adherence between the implants and the bone was recorded for eight implants with titanium hydride coating and four implants that had only been cleaned and autoclaved. The adherence was determined by measuring the torque force (Ncm) needed to loosen the implants from the femur of the rabbits. The results are shown in table 1 below.

TABLE 1

|  | Removal torque (Ncm) | | | | | | | | ± SD | Mean |
|---|---|---|---|---|---|---|---|---|---|---|
| Implants of the invention | 45.1 | 52.5 | 36.2 | 53.5 | 83.2 | 59.1 | 87.6 | 68.2 | 18.0 | 60.7 |
| Reference implants | 10.2 | 12.3 | 14 | 17.5 | — | — | — | — | 3.1 | 13.5 |

From the table, it is evident that the implants with a surface layer of titanium hydride had a much better adherence than those without. Histology showed normal cells in contact with titanium hydride.

Example 3

Strength and stability of interface between metal and bone is critical to the long-term performance of load bearing implants in particular bone with poor quality. Data has been presented that rough surfaces induce better bone response, however the ideal type and degree of roughness remains unknown.

In this example the bone response to titanium with different surface roughness expressed by bone to implant retention was investigate. A test model was developed using coin shaped commercial pure (c.p.) titanium implants. With this model, further described below, the effect of the frictional forces during pull-out test is minimised. Different surface structures were obtained by grit-blasting with $TiO_2$, using different grain sizes.

The implants had the shape of disks, and they were machined from a 10 mm round bar of grad 2 titanium (ASTM B 348). The size of the disks was 6,25±0,01 mm in diameter with a thickness of 2.0±0,05 mm.

All disks were standardised with grinding disc from #800 to #1200 grit size and polished with 6μ diamond abrasive, according to Struers® Metalog Guide before further treatments.

All disks were pre-treated with trichloroethylene in an ultrasonic bath for 30 min, rinsed with ethanol then ethanol in ultrasonic bath for 3×10-min, and finally rinsed with deionized water.

A total of forty-eight implants were divided into three groups: Group 1: implants with electropolished surfaces, Group 2: implants that were blasted with $TiO_2$ particles with a grain size of 22–28 μm, and Group 3: implants that were blasted with $TiO_2$ particles with a grain size of 180–220 μm. Eight implants in each group were used as controls, while the other eight in each group were treated according to the invention. Four implants, one from each group were randomly in-operated into the tibial bone of each of the twelve New Zealand White rabbits. Before surgery, the rabbits were given Fentanyl/fluanison (Hypnorm®) 0,05–0,1 ml/kg s.c. 10 minutes prior to being removed from their cages. The operation sites were depilated and washed with soap and ethanol prior to a sterile cover of the lover part of the rabbit. The rabbits were anaesthetised with Midazolam (Dormicum®) 2 mg/kg bw i.v. If the animals started to show signs of waking up between 0,1 to 0,5 diluted Hypnorm® (1 ml Hypnorm® and 9 ml sterile water) was injected i.v. slowly until an adequate effect was obtained. Local-anaesthesia, Lidocain (Xylocain/adrenaline®) 1,8 ml s.p. in joint site, tuberositas tibiae, was used. The animals were placed on the operation table on their back, covered with sterile cloths prior to disinfection with 70% etanol. Their eyes were protected for drying with ointment.

Two implants were placed in each proximal tibia. An incision of 5 cm was made on the medial-anterior part of tibiae, starting approximately 2 cm from patella. The incision penetrated epidermis, dermis and the facial layers. Lateral reflection of these tissues exposed the underlying periosteum. Additional medial-anterior incision was made through the periosteum. A 1,0-mm diameter twist drill (Medicon®) in a handle was used to get two guide holes with 8 mm distance. A 6,65 mm diameter stainless steel bur in a slow-speed handpiece with physiological saline solution irrigation was used to get flat cortical surfaces for the implants and the individually fitted Teflon caps, which were used to cover the implants to prevent bone overgrowth. Care was taken to prevent breaching the cortical bone. Two implants were placed on the even prepared surface of the cortical bone. To stabilise the implants a titanium-plate (Medicon® CMS) in proximal-distal direction, were retained with two titanium screws. The facial layers were repositioned and sutured with 4-0 polyglycolic acid suture. The superficial layers were sutured using an intra cutanos technique with the same 4-0 suture.

After surgery, each animal received an injection with 20 ml NaCl infusion s.c. and 0,05 mg Temgesic® "Reckitt & Colman" 0,02–0,05 mg/kg s.c.

As post op analgesic the animals received 0,05 mg Temgesic® for four days.

Observation time was set for 8 weeks. The fixation of the implants to bone was then evaluated using a pull-out test. The rabbits were sacrificed with an over-dose i.v. and an intracardiac injection with Pentobarbital (Mebumal®) while under sedation with Hypnorm®.

Immediately after euthanisation the superficial tissues overlying the implants were removed to expose the Teflon caps. The titanium plate was carefully removed and the Teflon cap separated from the implants using pressure-air. Tibia was cut in the knee joint and fixated in a special designed jig, which was anchored to the bed of the testing machine to stabilise the bone during the pull-out procedure. A metal pin with a "ball" in one end and threads in the other was fastened in pre-threads implants.

The equipment used to apply pull-out force was Lloyds LRX Materials Testing machine. The ball-attachment on the metal pin was fit in a holder connected to a load cell of 500 N. This attachment was designed to avoid any shear and tilt forces on the implant and tolerates for the axis of the implant not being precisely perpendicular on the bone surface. Crosshead speed range was set to 1,0 mm/min. Force measuring accuracy was set to +/−1%.

Figure 2:
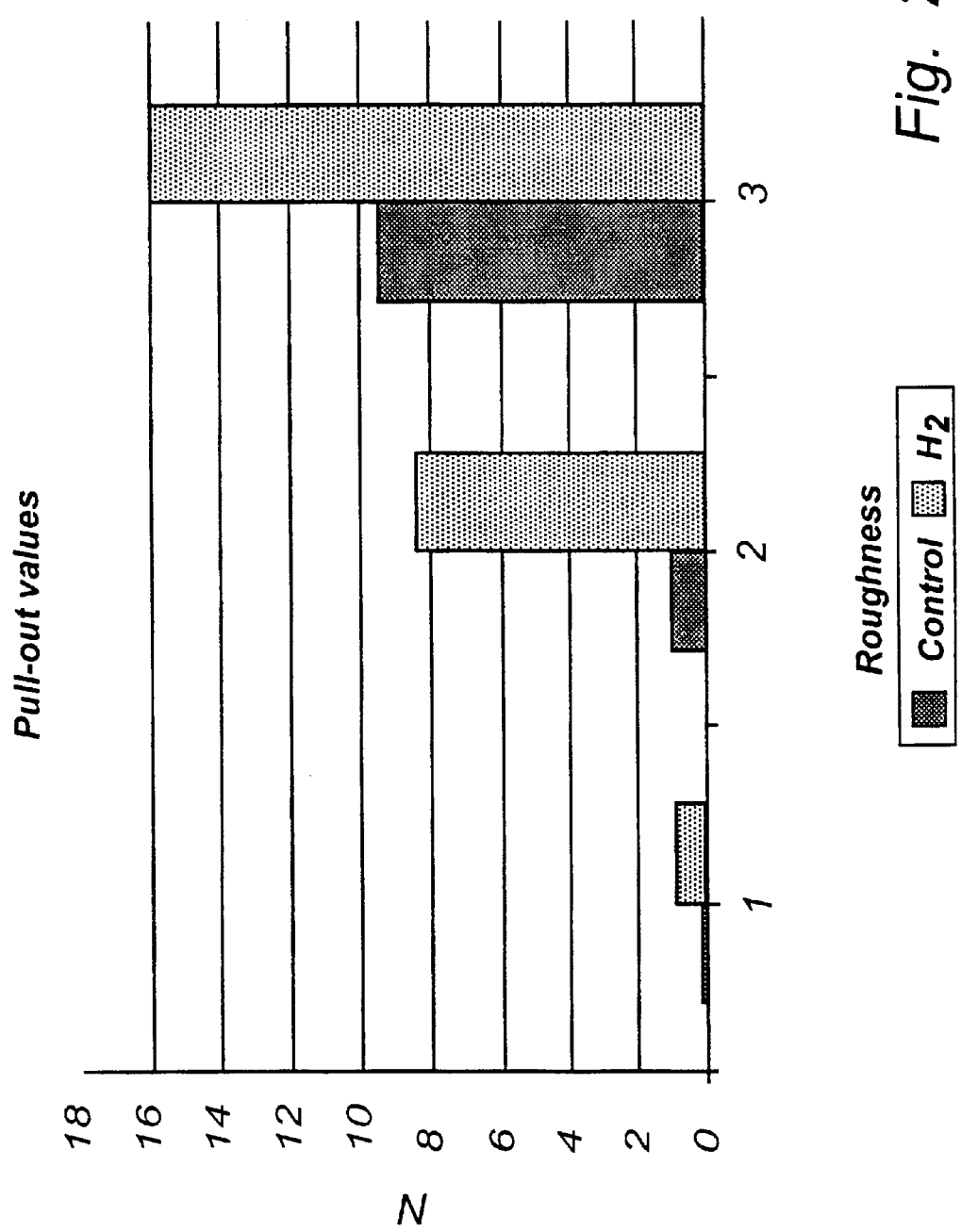
FIG. 2 illustrates the forces necessary to pull out implants according to the invention compared to control implants, from the tibia of rabbits (see Example 4).

The results of the pull-out test are shown in FIG. 2.

It is evident that the implants according to the invention, i.e. the implants with hydrided surfaces, showed a better bone fixation than the controls.

What is claimed is:

1. A sterile implant with a surface modified for improved biocompatibility and consisting of a metal or an alloy thereof, characterized in that the surface of the sterile implant comprises a hydrided outer layer.

2. An implant according to claim 1, wherein said metal is titanium, zirconium, hafnium or tantalum.

3. An implant according to claim 2, wherein said modified outer layer consists of a hydride of titanium, zirconium, hafnium or tantalum.

4. An implant according to claim 3, wherein said metal is titanium.

5. An implant according to claim 4, wherein said hydrided outer layer consists of a titanium hydride.

6. An implant according to claim 1, wherein the implant surface comprises a geometrical modification of the outer layer.

7. A biocompatible implant according to claim 1 intended for implanting into living organisms.

8. A biocompatible implant according to claim 7 intended for replacement of lost or damaged body parts.

9. A biocompatible implant according to claim 7 intended for restoring function of lost or damaged body parts.

10. A biocompatible implant according to claim 7, wherein said implant is a dental implant.

11. A biocompatible implant according to claim 7, wherein said implant is an orthopedic implant.

12. A method for the production of a biological implant according to claim 1, wherein a core of a metal or an alloy thereof is coated with a surface layer of a metal hydride, and the coated core is sterilised.

13. A method according to claim 12, wherein said metal is titanium, zirconium, hafnium or tantalum.

14. A method according to claim 13, wherein said metal hydride is a hydride of titanium, zirconium, hafnium or tantalum.

15. A method according to claim 12, wherein said metal is titanium.

16. A method according to claim 15, wherein said metal hydride is a titanium hydride.

17. A method according to claim 12, wherein said core of a metal is a starting implant of titanium or an alloy thereof.

18. A method according to claim 12, wherein said core of a metal is treated by electrolysis thereby converting the surface region one or more hydrides of the metal or alloy thereof constituting the core.

19. A method according to claim 18, wherein said core of a metal, constituting a cathode, is placed in an electrolytic bath.

20. A method according to claim 19, wherein said bath is an acid aqueous solution of NaCl.

21. A method according to claim 20, wherein said bath has a pH-value below 4 and a temperature of at least 40° C.

22. A method according to claim 21, wherein the temperature of the bath is at least 80° C.

23. A method according to claim 19, wherein the pH-value of the bath is adjusted by addition of at least one acid selected from the group consisting of HCl, $H_2SO_4$, $HNO_3$ and $HClO_4$.

24. A method according to claim 23, wherein said bath is an aqueous solution comprising 0.05–1 M NaCl and $3 \cdot 10^{-4}$–2 M of the acid.

25. A method according to claim 18, wherein the density of the current used to perform the electrolysis is 0.1–10 $mA/cm^2$.

26. A method according to claim 12, wherein the surface roughness of the titanium hydride layer is increased.

27. A method according to claim 26, wherein the surface roughness is increased by blasting the implant.

28. A method according to claim 12, wherein the implant is etched in a bath consisting of an aqueous solution comprising fluorine ions in a concentration of 0.2–10 M, said bath having a pH-value of 3.3–7.

29. A method according to claim 12, wherein the implant produced is intended for osseointegration.

30. A method according to claim 12, wherein the implant produced is a dental implant.

31. An implant which is implanted in biological tissue and in direct contact with said tissue, said implant consisting of a metal or an alloy thereof, wherein the surface of the implant comprises a hydrided outer layer to provide improved biocompatibility.

32. An implant according to claim 31, wherein said metal is titanium, zirconium, hafnium or tantalum.

33. An implant according to claim 32, wherein said modified outer layer consists of a hydride of titanium, zirconium, hafnium or tantalum.

34. An implant according to claim 32, wherein said metal is titanium and said hydrided outer layer consists of a titanium hydride.

35. An implant according to any one of claims 32–34, wherein the implant surface comprises a geometrical modification of the outer layer.

36. An implant according to any one of claims 32–34, wherein said tissue is dental tissue.

37. An implant according to any one of claims 32–34, wherein said tissue is bone tissue.

* * * * *